United States Patent [19]

Jang et al.

[11] Patent Number: 5,508,381

[45] Date of Patent: Apr. 16, 1996

[54] PROCESS FOR PREPARING HIGHLY WATER ABSORBENT RESIN

[75] Inventors: Tae-Hwan Jang; Su-Beom Choi; Hyung-Mann Lee; Myung-Joong Kim, all of Daejeon, Rep. of Korea

[73] Assignee: Lucky Limited, Seoul, Rep. of Korea

[21] Appl. No.: 260,182

[22] Filed: Jun. 15, 1994

Related U.S. Application Data

[63] Continuation-in-part of Ser. No. 947,164, Sep. 18, 1992, abandoned.

[30] Foreign Application Priority Data

Sep. 20, 1991 [KR] Rep. of Korea ............... 91-16576
Jan. 17, 1992 [KR] Rep. of Korea ............... 92-640

[51] Int. Cl.$^6$ ........................................ C08L 33/02
[52] U.S. Cl. ........................... 525/119; 604/372
[58] Field of Search ............................... 525/119

[56] References Cited

U.S. PATENT DOCUMENTS

| | | | |
|---|---|---|---|
| 4,497,930 | 2/1985 | Yamasaki | 525/54.24 |
| 4,541,871 | 9/1985 | Obayashi | 525/125 |
| 4,735,987 | 4/1988 | Morita | 524/436 |
| 5,314,952 | 5/1994 | Choi | 525/119 |

FOREIGN PATENT DOCUMENTS 223203 10/1987 Japan ........................ 525/119

*Primary Examiner*—John C. Bleutge
*Assistant Examiner*—D. R. Wilson
*Attorney, Agent, or Firm*—Baker & Daniels

[57] ABSTRACT

The present invention provides an improved process for preparing a highly water absorbent resin having a superior suction power and excellent gel strength, which consists essentially of:

(1) neutralizing acrylic acid to a neutralization degree ranging from 50 to 100% based on the total number of moles of the acid employed and polymerizing it by a reverse phase suspension polymerization to provide a neutralized polymer;

(2) dehydrating the polymer until its water content reaches 25% by weight or less based on the weight of the polymer through an azeotropic distillation thereof in the presence of a lipophilic solvent;

(3) crosslinking the dehydrated polymer in the presence of a hydrophilic crosslinking agent containing at least two epoxy groups in an amount ranging from 0.05 to 5.0% by weight and water added in an amount ranging from 7.0 to 25.0% by weight based on the weight of the dehydrated polymer;

(4) dehydrating the crosslinked polymer until 60% by weight or more of the amount of water added in step(3) above is removed through an azeotropic distillation thereof under reflux; and (5) recovering the crosslinked and dehydrated polymer by filtration.

3 Claims, No Drawings

5,508,381

PROCESS FOR PREPARING HIGHLY WATER ABSORBENT RESIN

REFERENCE TO RELATED APPLICATION

This is a continuation-in-part of application Ser. No. 07/947,164 filed on Sep. 18, 1992, now abandoned.

FIELD OF THE INVENTION

The present invention relates to a process for preparing a water absorbent resin; and, particulary to a process for preparing a highly water absorbent resin having a superior suction power and excellent gel strength.

BACKGROUND OF THE INVENTION

Many water absorbent materials including natural materials (e.g., sponge, pulp and paper) and synthetic materials (which may be prepared by partially neutralizing a hydrous polymer having a hydrophilic group, e.g., —OH, —NH$_2$ or —COOH, with a salt) have been used conventionally as sanitary materials and in the agricultural field. However, since they absorb water or other fluids through a physical process, they tend to have a low water absorption capacity and, consequently, they have a limited ability to retain the water absorbed especially when pressure is applied.

To improve the absorption capacity, therefore, various synthetic absorbent materials which can attract water through both physical and chemical mechanisms have been developed; and, representative examples thereof include a partially crosslinked polyacrylic salt, saponificated starch-acrylonitrile graft copolymer, crosslinked cellulose-acrylic acid salt graft copolymer, etc. They are useful as sanitary materials such as diapers and sanitary napkins, and in a civil engineering and gardening field. They are also useful in other fields such as coagulation of sludges, dehydration of oils and prevention of dew condensation in contruction materials.

Hithereto, many such improved water absorbent resins useful as sanitary materials have been developed. However, in the sanitary materials field, particulary disposable diapers and menstrual napkins, it is very important for the water absorbent resin employed to have a good suction power and gel strength.

The suction power as used herein means the force of sucking water from pulp that has absorbed water; and the gel strength means the stability of the fluid-absorbed state.

U.S. Pat. No. 4,497,930 discloses a method for preparing an absorbent polymer, which comprises: polymerizing reaction monomers; dehydrating the resultant hydrophilic polymer to provide a water content ranging from 10 to 40% by weight based on the total amount of the hydrophilic polymer; and crosslinking said hydrophilic polymer in the presence of a crosslinking agent having at least two functional groups in the molecule, which are capable of reacting with carboxyl or carboxylate groups. However, in this method, since the crosslinking agent is added together with water in an amount that can barely dissolve the crosslinking agent therein, its presence tends to be limited on the surface of the polymer. Therefore, although the water absorption capacity and absorption rate of the polymer may be good, the suction power and gel strength tend to be low.

U.S. Pat. No. 4,541,871 discloses also a method for preparing an absorbent resin, which comprises: crosslinking a resin having a carboxylate group with 0.005–5% by weight of a crosslinking agent, in the presence of water in a proportion ranging from 0.01 to 1.3 parts by weight per part by weight of the resin. In this method, since water is removed in an amount of less than 0.5 parts by weight on the basis of the added amount of water during the dehydration process, the resultant resin has a poor suction power and gel strength.

As described in the above, the absorbent resins prepared by the methods described in the above-mentioned patents may have good water absorption capacity and absorption rate, but have poor suction power and gel strength to be useful for sanitary materials.

SUMMARY OF THE INVENTION

Accordingly, it is an object of the present invention to provide a process for preparing a highly water absorbent resin having a superior suction power and gel strength.

In accordance with one aspect of the invention, there is provided a process for preparing a highly water absorbent resin, which consists essentially of:

(1) neutralizing acrylic acid to a neutralization degree ranging from 50 to 100% based on the total number of moles of the acid employed and polymerizing it by a reverse phase suspension polymerization to provide a neutralized polymer;

(2) dehydrating the polymer until its water content reaches 25% by weight or less based on the weight of the polymer through an azeotropic distillation thereof in the presence of a lipophilic solvent;

(3) crosslinking the dehydrated polymer in the presence of a hydrophilic crosslinking agent containing at least two epoxy groups in an amount ranging from 0.05 to 5.0% by weight and water added in an amount ranging from 7.0 to 25.0% by weight based on the weight of the dehydrated polymer;

(4) dehydrating the crosslinked polymer until 60% by weight or more of the amount of water added in step (3) above is removed through an azeotropic distillation thereof under reflux; and (5) recovering the crosslinked and dehydrated polymer by filtration.

During the above process, the water can penetrate into the polymer accompanied with the crosslinking agent; and, as the result, the crosslinking agent can be present on the surface of the polymer in a greater amount while inside of the polymer in a smaller amount. Thereafter, when the crosslinked polymer is dehydrated at the boiling point of the solvent, the degree of crosslinkage on the surface of the polymer becomes high and the degree of the crosslinkage of inside of the polymer becomes low; and, as the result, a highly water absorbent resin having an excellent suction power and gel strength can be obtained.

In accordance with another aspect of the invention, there is provided a process for preparing an absorbent resin, which further comprises, between step (4) and step (5), a secondary crosslinking of the polymer crosslinked in step (3) in the presence of a mixture of a hydrophilic crosslinking agent and a hydrophilic solvent after removing the lipophilic solvent present and a dehydration of the secondarily crosslinked polymer by using an azeotropic distillation method.

During the secondary crosslinking process, the hydrophilic solvent is mainly present on the surface of the polymer together with the crosslinking agent, which makes the degree of crosslinkage on the surface of the polymer becomes more higher than that of inside of the polymer when the polymer is dehydrated at the boiling point of the solvent; and, as the result, a highly water absorbent resin having a superior suction power can be obtained.

DETAILED DESCRIPTION OF THE INVENTION

The monomers or polymers containing a carboxyl or carboxylate group employed in the present invention may include: monomers such as acrylic acid and methacrylic acid; graft polymers prepared by grafting acrylic acid with starch, cellulose, agarose or chitin; and copolymers prepared by copolymerizing acrylic acid or methacrylic acid with maleic acid, acrylamide, 2-acrylamido-2-methylpropane sulfonic acid or 2-hydroxyethyl methacrylate.

The neutralization of such monomers or polymers may be carried out by using an alkali metallic hydroxide, preferably sodium hydroxide and at a degree of neutralization ranging from 50 to 100%, preferably 60 to 80% based on the total moles of the monomers or polymers employed. For the neutralization, such monomers or polymers may be dissolved (or suspended) to be a 20 to 70%, preferably 40 to 60% aqueous solution.

Such monomers may be polymerized by a reversed phase suspension polymerization method in the presence of a lipophilic solvent. Examples of the useful lipophilic solvent may include: an aliphatic or aromatic solvent having a boiling point ranging from 30° to 200° C. for example, n-hexane, n-heptane, benzene, xylene, toluene, cyclopentane and cyclohexane, which is preferred. The lipophilic solvent may be employed in an amount ranging from 0.1 to 50 parts by weight, preferably 0.5 to 30 parts by weight per one part by weight of the monomers or polymers employed.

During the polymerization process, a surfactant and a polymerization initiator may be employed. Examples of the surfactant may include sorbitan monolaurate having a hydrophilic-lipophilic balance(HLB) ranging from 8 to 12. The polymerization initiator may be an aqueous radical polymerization initiator; and examples thereof may include: ammonium persulfate, potassium persulfate, which is preferred, and hydrogen peroxide. The initiator may be introduced alone or in combination with two or more.

The polymer obtained by partial neutralization and polymerization is then dehydrated by using an azeotropic distillation method during or after the polymerization process. The water content of the resultant polymer should be adjusted within 25% by weight or less based on the weight of the polymer, in accordance with the present invention.

The crosslinking agent employed in the crosslinking procedure should be hydrophilic or water-soluble and preferably have at least two epoxy groups, which can react with carboxyl or carboxylate groups. Representative examples of the crosslinking agent may include: ethylene glycol diglycidyl ether, glycerol polyglycidyl ether, trimethylol propane polyglycidyl ether and sorbitol polyglycidyl ether with ethylene glycol diglycidyl ether being preferred. The crosslinking agent may be suitably employed in an amount ranging from 0.05 to 5.0% by weight based on the weight of the polymer, although the amount largely depends on the crosslinking agent and the polymer employed.

In order to obtain a highly water absorbent resin having a superior suction power and gel strength, water should be added along with the crosslinking agent in the crosslinking reaction in an amount ranging from 7.0 to 25.0% by weight based on the weight of the dehydrated polymer and preferably removed during the subsequent dehydration process in an amount of 60% by weight or more based on the added amount of water.

In another embodiment of the present invention as described above, the water absorbent resin may be prepared by a method further comprising a secondary crosslinking of the crosslinked polymer in the presence of a mixture of a hydrophilic crosslinking agent and a hydrophilic solvent after having removed the lipophilic solvent and a dehydration of the secondarily crosslinked polymer by using an azeotropic distillation method.

The secondary crosslinking process can be conducted at the boiling point or higher of the hydrophilic solvent. The hydrophilic crosslinking agent may be used in an amount ranging from 0.5 to 5.0% by weight based on the weight of the polymer; and, the hydrophilic solvent may be used in an amount ranging from 1.7 to 2.7 parts by weight per one part by weight of the polymer. Suitable examples of the hydrophilic solvent may include methanol and ethanol with methanol being preferred.

The crosslinked polymer so prepared may be recovered by filtration followed by drying as known in the art.

The following Examples are intended to illustrate the present invention more specifically without limiting the scope of the invention.

As for the water absorbent resin prepared in Examples and Comparative Examples, the suction power(in ml/g) was evaluated by measuring the sucked amount of water in the resin in 0.9% NaCl aqueous solution for 1,2,3,4 or 5 minutes. The absorption capacity was evaluated as follows: 1 g of the resin was introduced into 0.9% NaCl aqueous solution; and, 30 minutes thereafter, the gel produced was filtered by using 80 mesh screen and weighed. The gel strength was measured by pressing the resin which has been saturated with deionized water by a hand.

EXAMPLE 1

In a 500 ml four-necked, round-bottomed flask equipped with a stirrer, a Dean-Stark apparatus, a reflux condenser, a pressure controlled funnel and a nitrogen inlet tube were charged 160 g of cyclohexane and 1.0 g of Ryoto sugar ester surfactant S-970(HLB=9.0) (a product of Mitsubishi Food Corporation) in oil bath. The reaction flask was purged with nitrogen to remove oxygen; and the bath temperature was increased to 75° C.

In a 200 ml flask containing 30.9 g of acrylic acid was slowly charged 49.1 g of aqueous sodium hydroxide solution (containing 9.2 g of NaOH) with cooling to produce a 45% solid contented solution, which shows that the acrylic acid was neutralized in a degree of 60% based on the moles thereof. 0.1 g of potassium persulfate dissolved in 3 g of distilled water was added thereto with stirring. The resulting solution was added dropwise to the above-mentioned 500 ml flask containing cyclohexane and surfactant through the pressure controlled funnel; and, the mixture was reacted to produce a polymer. The bath temperature was increased to 90° C.; and 38 g of water was removed by an azeotropic distillation so as to provide a water content of 20% by weight in the resultant polymer. Thereafter, 0.2 g of ethylene glycol diglycidyl ether dissolved in 5 g of water was added to crosslink the polymer. The crosslinking reaction was continued until 5 g of water was removed using the Dean-Stark apparatus. Upon the completion of the reaction, the resulting polymerized mixture was vaporized to dry under a reduced pressure to obtain a dry polymer, whose suction power, absorption capacity and gel strength were evaluated. The evaluation results are shown in Table 3.

EXAMPLES 2 to 5

The procedures described in Example 1 were repeated except the amount of water employed in dissolving the crosslinking agent for the crosslinking reaction and the amount of water removed during the dehydration process, which varified as shown in Table 1. The evaluation results of the polymer resin thus prepared are shown in Table 3.

TABLE 1

| Example No. | Water Employed (g) | Water Removed (g) |
| --- | --- | --- |
| 2 | 5 | 10 |
| 3 | 6 | 11 |
| 4 | 7 | 12 |
| 5 | 9 | 14 |

EXAMPLE 6

The procedures described in Example 1 were repeated except that a solution of 0.5 g of ethylene glycol diglycidyl ether dissolved in 6 g of distilled water was employed; and, during the dehydration process, 5 g of water was removed. The evaluation results of the polymer resin thus prepared are shown in Table 3.

EXAMPLE 7

In a 500 ml four-necked, round-bottomed flask equipped with a stirrer, a Dean-Stark apparatus, a reflux condenser, a pressure controlled funnel and a nitrogen inlet tube, were charged 160 g of cyclohexane and 1.0 g of Ryoto sugar ester surfactant S-970(HLB=9.0) in oil bath. The reaction flask was purged with nitrogen to remove oxygen; and, the bath temperature was increased to 75° C.

In a 200 ml flask containing 30.9 g of acrylic acid was slowly charged 49.1 g of aqueous sodium hydroxide solution (containing 9.2 g of NaOH) with cooling to produce a 45% solid contented solution. A solution of 0.1 g of potassium persulfate dissolved in 3 g of distilled water was added thereto with stirring. The resulting solution was added dropwise to the above-mentioned 500 ml flask containing cyclohexane and the surfactant through the pressure controlled funnel; and, the mixture was reacted to produce a polymer. The bath temperature was increased to 90° C.; and 38 g of water was removed by an azeotropic distillation so as to provide a water content of 20% by weight in the resultant polymer. Thereafter, a solution of 0.2 g of ethylene glycol diglycidyl ether dissolved in 3 g of water was added to crosslink the polymer. The crosslinking reaction was continued until 5 g of water was removed using the Dean-Stark apparatus. After the completion of the reaction, the cyclohexane solvent was removed therefrom and a mixture of 0.3 g of ethylene glycol diglycidyl ether and 100 g of methanol was added thereto. The reaction solution was refluxed at 90° C. for 2 hours. The resulting polymerized mixture was filtered to remove the methanol solvent and vaporized to dry under a reduced pressure to obtain a dry polymer, whose suction power, absorption capacity and gel strength were evaluated. The evaluation results are shown in Table 3.

EXAMPLES 8 to 10

The procedures described in Example 7 were repeated except the amount of water employed in dissolving the crosslinking agent and the amount of methanol employed for the secondary crosslinking process, which varified as shown in Table 2. The evaluation results of the polymer resin thus prepared are shown in Table 3.

TABLE 2

| Example No. | Water Employed (g) | Methanol Employed (g) |
| --- | --- | --- |
| 8 | 5 | 100 |
| 9 | 5 | 80 |
| 10 | 10 | 100 |

EXAMPLE 11

The procedures described in Example 8 were repeated except that, in the secondary crosslinking process, a solution of 0.5 g of ethylene glycol diglycidyl ether dissolved in 100 g of methanol was employed. The evaluation results of the resulting polymer resin are shown in Table 3.

EXAMPLE 12

The procedures described in Example 8 were repeated except that, in the first crosslinking process, a solution of 0.5 g of ethylene glycol diglycidyl ether dissolved in 5 g of water was employed. The evaluation results of the resulting polymer resin are shown in Table 3.

COMPARATIVE EXAMPLE 1

In a 500 ml four-necked, round-bottomed flask equipped with a stirrer, a Dean-Stark apparatus, a reflux condenser, a pressure controlled funnel and a nitrogen inlet tube were charged 160 g of cyclohexane and 1.0 g of Ryoto sugar ester surfactant S-970(HLB=9.0) in oil bath. The reaction flask was purged with nitrogen to remove oxygen; and the bath temperature was increased to 75° C.

In a 200 ml flask containing 30.9 g of acrylic acid was slowly charged 49.1 g of aqueous sodium hydroxide solution (containing 9.2 g of NaOH) with cooling to produce a 45% solid contented solution. A solution of 0.1 g of potassium persulfate dissolved in 3 g of distilled water was added thereto with stirring. The resulting solution was added dropwise to the above-mentioned 500 ml flask containing cyclohexane and the surfactant through the pressure controlled funnel; and the mixture was reacted to produce a polymer. The bath temperature was increased to 90° C.; and 38 g of water was removed by an azeotropic distillation so as to provide a water content of 20% by weight in the resultant polymer. After the completion of the reaction, the resulting polymerized mixture was cooled to room temperature, filtered and dried to obtain a polymer whose suction power, absorption capacity and gel strength were evaluated. The evaluation results are also shown in Table 3.

COMPARATIVE EXAMPLE 2

The procedures described in Comparative Example 1 were repeated: except that, after the azeotropic distillation process, 0.2 g of ethylene glycol diglycidyl ether was added and then the reactants were refluxed for 2 hours. The evaluation results are also shown in Table 3.

COMPARATIVE EXAMPLE 3

The procedures described in Comparative Example 1 were repeated except that, after the azeotropic distillation process, a solution of 0.2 g of ethylene glycol diglycidyl ether dissolved in 1 g of water was added and then the reactants were refluxed for 2 hours. The evaluation results are also shown in Table 3.

COMPARATIVE EXAMPLE 4

The procedures described in Comparative Example 1 were repeated except that, after the azeotropic distillation process, cyclohexane was removed therefrom and a solution of 0.2 g of ethylene glycol diglycidyl ether dissolved in 160 g of methanol was added, and then the reactants were refluxed for 2 hours. The evaluation results are also shown in Table 3.

COMPARATIVE EXAMPLE 5

The procedures described in Comparative Example 1 were repeated except that, after the azeotropic distillation process, cyclohexane was removed therefrom and 160 g of methanol was added. Subsequently, a solution of 0.5 g of ethylene glycol diglycidyl ether dissolved in 15 g of water was added and then the reactants were refluxed for 2 hours. The evaluation results are also shown in Table 3.

COMPARATIVE EXAMPLE 6

The procedures described in Comparative Example 1 were repeated except that, after the azeotropic distillation process, cyclohexane was removed therefrom and a solution of 0.3 g of ethylene glycol diglycidyl ether dissolved in 100 g of methanol was added, and then the reactants were refluxed for 2 hours. The evaluation results are also shown in Table 3.

COMPARATIVE EXAMPLE 7

The procedures described in Example 7 were repeated except that the dehydration process by an azeotropic distillation was conducted to provide a polymer having the water content of 45% by weight. The evaluation results are also shown in Table 3.

COMPARATIVE EXAMPLE 8

The procedures described in Comparative Example 1 were repeated except that, after the azeotropic distillation process, cyclohexane was removed therefrom and 100 g of methanol was added. Subsequently, a solution of 0.3 g of ethylene glycol diglycidyl ether dissolved in 15 g of water was added and then the reactant was refluxed for 2 hours. The evaluation results are also shown in Table 3.

COMPARATIVE EXAMPLE 9

In a 200 ml flask was placed 30.9 g of acrylic acid, and 49.1 g of aqueous sodium hydroxide solution(containing 9.2 g of NaOH) was dropped thereinto with cooling and stirring to produce a solution having the solid content of 45%, which shows that the acrylic acid was neutralized to a degree of 60% based on the moles thereof. 0.1 g of potassium persulfate dissolved in 3 g of distilled water was added thereto with stirring at room temperature.

Into a 500 ml flask provided with a reflux condenser purged with nitrogen were charged 160 g of cyclohexane and 1.0 g of Ryoto sugar ester surfactant S-970(HLB=9.0) (a product of Mitsubishi Food Corporation). To the resulting solution was added dropwise the above-mentioned aqueous partially neutralized acrylic acid solution to form a suspension. The flask was again completely purged with nitrogen, the temperature of the suspension was elevated and polymerization was conducted for 3 hours while maintaining the bath temperature at 55°–60° C.; and 38 g of water was removed by an azeotrophic distillation so as to provide a water content of 20% by weight in the resultant polymer.

In a 500 ml flask provided with a stirrer, an oil bath and a cooler was placed the polymer thus obtained, and 150 g of cyclohexane and 0.2 g of ethylene glycol diglycidyl ether dissolved in 5 g of water was added thereto with stirring. The resulting mixture was well stirred and then evaporated to dryness by maintaining the oil bath at 110° C. to obtain an absorbent polymer.

The amounts of cyclohexane and water removed during the evaporation were 150 g and 2.3 g, respectively. That is, the ratio of cyclohexane/water removed was 150/2.3(98.5/1.5). The evaluation results are also shown in Table 3.

COMPARATIVE EXAMPLE 10

In a 500 ml flask provided with a stirrer, a reflux condenser, a dropping funnel and a nitrogen gas inlet pipe were placed 160 g of cyclohexane and 1.0 g of Ryoto sugar ester surfactant S-970(HLB=9.0).

In a 200 ml flask containing 30.9 g of acrylic acid was slowly charged 49.1 g of aqueous sodium hydroxide solution (containing 9.2 g of NaOH) with cooling to produce a solution having the solid content of 45%, which shows that the acrylic acid was neutralized to a degree of 60% based on the moles thereof. 0.1 g of potassium persulfate dissolved in 3 g of distilled water was added thereto with stirring. The resulting solution was added dropwise to the above-mentioned 500 ml flask containing cyclohexane and surfactant through a pressure controlled funnel; and, the mixture was reacted for 1.5 hours to produce a polymer.

The reaction flask was purged with nitrogen and the bath temperature was increased to 75° C. Thereafter, the water content of the polymer suspended in cyclohexane was adjusted to 20% by an azeotropic dehydration. Thereafter, 0.03 g of ethylene glycol diglycidyl ether dissolved in 1 ml of water was added thereto at 73° C. with stirring. The resulting solution was further held at that temperature for 2 hours. Then, cyclohexane was removed and the polymer obtained was dried under a reduced pressure at 80°–100° C. to obtain an absorbent polymer. The evaluation results are also shown in Table 3.

TABLE 3

| | | Suction Power (ml/g) | | | | | |
|---|---|---|---|---|---|---|---|
| | Absorption Capacity | 1 min | 2 min | 3 min | 4 min | 5 min | Gel Strength |
| Ex. 1 | 50 | 7.1 | 10.0 | 11.2 | 11.9 | 12.3 | ◯ |
| Ex. 2 | 55 | 9.6 | 12.2 | 13.6 | 14.5 | 15.2 | ◉ |
| Ex. 3 | 50 | 9.3 | 13.4 | 15.5 | 16.7 | 17.5 | ◉ |
| Ex. 4 | 60 | 9.4 | 11.5 | 12.7 | 13.5 | 14.0 | ◉ |
| Ex. 5 | 50 | 8.4 | 11.5 | 13.5 | 14.7 | 15.8 | ◉ |
| Ex. 6 | 45 | 12.6 | 16.5 | 17.9 | 18.6 | 19.0 | ◉ |
| Ex. 7 | 60 | 8.1 | 10.0 | 11.7 | 12.8 | 13.5 | ◉ |
| Ex. 8 | 58 | 9.5 | 12.1 | 13.4 | 14.2 | 14.9 | ◉ |
| Ex. 9 | 55 | 9.6 | 12.2 | 13.6 | 14.5 | 15.2 | ◉ |
| Ex. 10 | 53 | 10.1 | 10.7 | 13.7 | 14.3 | 14.8 | ◉ |
| Ex. 11 | 55 | 9.7 | 12.2 | 13.4 | 14.1 | 14.7 | ◉ |
| Ex. 12 | 50 | 12.1 | 15.3 | 16.7 | 17.5 | 18.4 | ◉ |

TABLE 3-continued

| | Absorption Capacity | Suction Power (ml/g) | | | | | Gel Strength |
| | | 1 min | 2 min | 3 min | 4 min | 5 min | |
| --- | --- | --- | --- | --- | --- | --- | --- |
| Comp. Ex. 1 | 120 | 0.4 | 0.6 | 0.8 | 1.0 | 1.1 | X |
| Comp. Ex. 2 | 95 | 2.7 | 3.4 | 3.8 | 4.0 | 4.2 | X |
| Comp. Ex. 3 | 84 | 3.4 | 4.6 | 5.4 | 5.6 | 5.8 | Δ |
| Comp. Ex. 4 | 90 | 1.1 | 1.4 | 1.6 | 1.8 | 2.0 | X |
| Comp. Ex. 5 | 74 | 2.1 | 3.9 | 4.4 | 5.0 | 5.4 | Δ |
| Comp. Ex. 6 | 90 | 1.1 | 1.4 | 1.6 | 1.8 | 2.0 | X |
| Comp. Ex. 7 | 35 | 7.1 | 9.9 | 10.9 | 11.3 | 11.6 | ⊚ |
| Comp. Ex. 8 | 82 | 3.1 | 3.9 | 4.4 | 5.0 | 5.4 | Δ |
| Comp. Ex. 9 | 52 | 5.8 | 8.7 | 10.0 | 10.8 | 11.2 | ○ |
| Comp. Ex. 10 | 82 | 3.1 | 4.2 | 4.8 | 5.1 | 5.5 | Δ |

⊚: difficult to break down even when high pressure is applied to it.
○: possible to break down when high pressure is applied to it.
Δ: easy to break down.
X: tacky and easy to break down even when low pressure is applied to it.

As shown in Table 3 above, the present invention provides a highly water absorbent resin with improved absorbing properties such as superior suction power and gel strength.

While the invention has been described in connection with the above specific embodiments, it should be recognized that various modifications and changes as may be apparent to those skilled in the art to which the invention pertains may be made and also fall within the scope of the invention as defined by the claims that follow.

What is claimed is:

1. A process for preparing a water absorbent resin, which consists essentially of:

(1) neutralizing acrylic acid with an aqueous alkali metal hydroxide to a neutralization degree ranging from 50 to 100% based on the total number of moles of the acid employed and polymerizing it by a reverse phase suspension polymerization to provide a 50 to 100% neutralized polymer;

(2) dehydrating the polymer until its water content reaches 25% by weight or less based on the weight of the polymer through an azeotropic distillation under reflux of a solvent selected from the group consisting of n-hexane, n-heptane, benzene, xylene, toluene, cyclopentane and cyclohexane;

(3) crosslinking the dehydrated polymer by adding a mixture of a hydrophilic crosslinking agent containing at least two epoxy groups in an amount ranging from 0.05 to 5.0% by weight and water in an amount ranging from 7.0 to 25.0% by weight, both amounts being based on the weight of the dehydrated polymer;

(4) dehydrating the crosslinked polymer until 60% by weight or more of the amount of water added in step (3) above is removed through a continued azeotropic distillation under reflux of the solvent present in step (2); and (5) recovering the crosslinked and dehydrated polymer by filtration.

2. The process of claim 1 wherein said alkali metal hydroxide is sodium hydroxide.

3. The process of claim 1 wherein the crosslinking agent is selected from the group consisting of ethylene glycol diglycidyl ether, glycerol polyglycidyl ether, trimethylol propane polyglycidyl ether and sorbitol polyglycidyl ether.

* * * * *